United States Patent
Vallejo, Jr. et al.

(10) Patent No.: US 9,850,522 B2
(45) Date of Patent: *Dec. 26, 2017

(54) ONE-STEP RAPID ASSAY FOR THE DETECTION OF INHIBITORS OF ENZYMES

(71) Applicant: ANP Technologies, Inc., Newark, DE (US)

(72) Inventors: Yli Remo Vallejo, Jr., Newark, DE (US); David Milunic, Newark, DE (US); Ray Yin, Newark, DE (US); Renee Street, Bel Air, MD (US); De Chen, Newark, DE (US)

(73) Assignee: ANP Technologies, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/762,914

(22) PCT Filed: Jan. 22, 2014

(86) PCT No.: PCT/US2014/012582
§ 371 (c)(1),
(2) Date: Jul. 23, 2015

(87) PCT Pub. No.: WO2014/116727
PCT Pub. Date: Jul. 31, 2014

(65) Prior Publication Data
US 2015/0368691 A1    Dec. 24, 2015

Related U.S. Application Data

(60) Provisional application No. 61/884,072, filed on Sep. 29, 2013, provisional application No. 61/755,663, filed on Jan. 23, 2013.

(51) Int. Cl.
*C12Q 1/46* (2006.01)
*G01N 33/558* (2006.01)
*C12Q 1/26* (2006.01)
*C12Q 1/42* (2006.01)
*C12Q 1/44* (2006.01)

(52) U.S. Cl.
CPC .............. *C12Q 1/46* (2013.01); *C12Q 1/26* (2013.01); *C12Q 1/42* (2013.01); *C12Q 1/44* (2013.01); *C12Y 301/01001* (2013.01); *C12Y 301/01007* (2013.01); *G01N 33/558* (2013.01); *G01N 2333/916* (2013.01)

(58) Field of Classification Search
CPC ..................................................... C12Q 1/46
See application file for complete search history.

(56) References Cited

U.S. PATENT DOCUMENTS 6,221,625 B1    4/2001   Ashihara et al.
2008/0085525 A1  4/2008   Van Herwijnen

OTHER PUBLICATIONS

Du et al. Analytical Chemistry, 2012, 84:1380-1385.*
Hadd et al., "Microfluidic . . . Inhibitors," Anal Chem 71:5206-5212, 1999.

* cited by examiner

*Primary Examiner* — Bin Shen
(74) *Attorney, Agent, or Firm* — MDIP LLC (57) ABSTRACT

A device and method for the rapid on-site detection of inhibitors of enzymes, such as acetylcholinesterase, is described wherein the device contains all reagents added to a sample pad containing dried releasable enzyme creating a reaction mixture wherein inhibitor deactivates the enzyme, while said reaction mixture travels via a longitudinal membrane to a distal porous pad containing a substrate for the enzyme. The reaction of the enzyme and the substrate results in a product that can generate a measurable signal such as color, fluorescence or luminescence to serve as a reporter. Signal that is generated at this reaction zone is inversely proportional to inhibitor concentration in the test sample. A device containing two such strips, one for a test sample, the other for a negative control fluid as an onboard comparator is described. A purpose-built reader or an illuminating device, such as, containing an incandescent light source, a diode, a UV light source or any other illumination source that is suitable for the reporter or mere visualization is used to determine the level of reporter.

18 Claims, 5 Drawing Sheets

ONE-STEP RAPID ASSAY FOR THE DETECTION OF INHIBITORS OF ENZYMES

The instant application is a 371 application of PCT Ser. No. US2014/012582 that was filed 22 Jan. 2014, which claims benefit to U.S. Ser. No. 61/755,663 filed 23 Jan. 2013 and to U.S. Ser. No. 61/884,072 filed 29 Sep. 2013.

FIELD OF THE INVENTION

The present invention relates in part to rapid on-site detection methods of enzyme-inhibiting compounds.

For example, the use of pesticides has contributed to significant improvement in agricultural efficiency and productivity over the last 60 years and in the control and eradication of disease-bearing insects and other pests. However, the overuse of such compounds has led to contamination of soil and, through agricultural runoff, drinking water sources. The organophosphate and carbamate classes of pesticides are examples of such compounds. These pesticides owe their effectiveness to their ability to inhibit the neurotransmitter enzyme, acetylcholinesterase (AChE), which regulates nerve impulses in many life forms, including humans. When this enzyme is inhibited by these pesticides, the victim begins to suffer from bradycardia, hypotension, hypersecretion, bronchoconstriction, GI tract hypermotility, and decreased intraocular pressure. Morbidity progresses to death in many cases as exposure levels are increased.

Many nerve agents used in chemical warfare are also acetylcholinesterase inhibitors. Examples of these are sarin, soman, tabun, VX, VE, VG, and VM. Exposure to or ingestion of pesticides and related neurotoxins has also been linked to chronic illnesses, such as, depression and Parkinson's disease.

The management of worker exposure and of the effects of such pesticides and nerve agents on the general population requires methods that provide ready detection of such exposure by testing, readily available samples, such as, blood, plasma, serum or other biological fluids. Such samples can be used to identify and to quantify the toxins by determining the degree of inhibition of the target enzymes, such as, AChE.

BACKGROUND OF THE INVENTION

The detection of AChE inhibitors has been conducted using colorimetric methods that are based on decrease in color development by a primary or secondary substrate after exposure of the enzyme to a liquid sample containing an inhibitor. An example of such is the colorimetric method commercialized by Abraxis which uses Ellman's color reagent as an indicator substrate. That method tests the activity of a measured amount of enzyme after it has been exposed to a water sample potentially containing an inhibitor. After such exposure, the enzyme is reacted with its primary substrate, acetylthiocholine. Active enzyme will hydrolyze acetylthiocholine to thiocholine which in turn reacts with dithio-bis-nitrobenzoate to produce an orange-colored product, 5-thio-2-nitrobenzoate.

That method, though widely used, is complex, needing a standard curve for each test run, requiring numerous fluid transfer pipetting steps, and using a multiplicity of reaction vessels. In addition, the enzyme is inhibited by many organophosphates in vivo only after the inhibitor undergoes a physiological oxidation (Mahmoud and Casida, 1998). Hence, to mimic the required physiological oxidation for toxicity, a sample pretreatment step using an oxidizing agent, such as, bromine or hypochlorite, followed by a quencher to neutralize excess unreacted oxidizer, is required. Only by pre-oxidizing the sample can most organophosphates be detected by such methods.

Current laboratory procedures based on the use of Ellman's reagent that are approved include the Michel, micro-Michel, pH stat. Ellman and micro-Ellman assays, as well as certain variations of those assays.

Although those assays represent the current standard in AChE inhibitor detection. Ellman's reagent-based methods are not easily converted to rapid on-site testing because of the methodological complexity, the numerous steps and reaction vessels required and the need to keep heat-labile reagents refrigerated.

Other methods to detect such inhibitors are laboratory-based liquid, or gas chromatography methods coupled with mass spectrometry which rely on expensive, bulky equipment and elution profiles for identification.

Hence, there is a need for a simplified and rapid point of use assay. The instant invention addresses those shortcomings in the art. The test method of interest is simplified as a single device requiring only the addition of a measured volume of sample.

SUMMARY OF THE INVENTION

To overcome the shortcomings in the art of detecting inhibitors or enzymes, such as, an esterase, such as, cholinesterase, such as, acetylcholinesterase (AChE), the instant invention relates to a simplified, rapid test employing a modular device, referred to as a ticket or a test strip, comprising a longitudinal testing device comprising a sample addition pad at one end of the device and an enzyme substrate pad at the other end of the device. The test strip comprises a porous fluid transfer membrane which runs the length of the device to enable fluid to travel from one end to the other, for example, from the sample pad to the substrate pad. The sample pad can be a porous membrane material that is treated with proteins, sugars, and similar substances to coat internal and external surfaces with such substances to passivate such surfaces to prevent binding enzyme and other molecules relevant or involved in the reactions of interest. After such treatment, these sample pads are dried in an oven and then treated with a fixed uniform amount of enzyme in a buffer solution. After a second round of drying, these pads will contain enzyme molecules which are released from the pad matrix on addition of an aqueous sample. In contact with this sample pad is one end of a longitudinal length of porous fluid transfer membrane. At the other end of the longitudinal length of porous fluid transfer membrane is another porous pad, which previously had been treated with a fixed uniform amount of enzyme substrate in liquid solution, then dried. The enzyme substrate directly or indirectly generates a detectable and measurable signal, such as, fluorescence or color, on reaction with the enzyme.

The fluid sample can be, for example, an environmental fluid sample, such as, a water, which can be any water, such as, for human consumption, such as, processed drinking water, source water from natural and man-made or artificial bodies of water, such as, ponds and wells, lakes, rivers or oceans, water-based or water/organic washes or extracts of edible products, such as, fruits, vegetables, produce, meats and seafood, a dissolved or soluble sample of a wipe, swipe or an extract from a sampling, of a suspected contaminated surface, and so on. A wash of a solid, such as, an edible product comprises a liquid exposed to the solid or, for example, the edible product. A wipe or swipe comprises an absorptive or adsorptive material exposed to a surface, which absorptive or adsorptive material is exposed or suspended in a liquid and that liquid is then tested in a device and method of interest. Such fluid samples can potentially contain an enzyme inhibitor. Essentially any fluid sample can be tested with a device of interest.

A fixed uniform volume of a fluid sample suspected of containing an inhibitor is added to a sample pad of the test strip. The fluid sample dissolves the dried enzyme within the sample pad, enabling interaction of the enzyme with any inhibitor that may be present in the sample. The reaction mixture comprising the fluid potentially containing an inhibitor and the dissolved enzyme then contacts the porous fluid transfer membrane and flows along the longitudinal length of the fluid transfer membrane to the distal end thereof where the substrate pad is located. From the time the fluid dissolves the enzyme and as the reaction mixture travels downstream to the substrate pad, any inhibiting compound present in the sample interacts with enzyme active sites to disable activity of the enzyme. When the fluid reaches and saturates the substrate pad, any active enzyme in the fluid mixture then can react with the reporter substrate molecules contained therein resulting in a measurable signal, such as, fluorescence or color on or at the pad. In the presence of an inhibitor in the original fluid sample, some or all of the enzyme that reaches the substrate pad would be inactivated or poisoned by the inhibitor and will generate significantly diminished signal or no signal at all as compared to that generated by an uninhibited enzyme.

The signal generated at the substrate pad can then be measured by a reader and compared to a stored reference signal value representing an uninhibited enzyme. Alternatively, the test results can be assessed visually when a suitable reporter is used, such as, a substrate that yields a colored or a light reaction product.

In other embodiments, plural test strips, such as, two separate test strips can together comprise a single device. One test strip can be used to test a suspicious fluid that may contain an inhibitor, while the other test strip can simultaneously run a control fluid as a comparator. At the end of the test run, the signal of the test device is compared with that of the control device. In the case of no inhibitor in the test sample, both tests will show the same level of signal within a statistically established variation range. The signals can be measured and compared using, for example, a purpose-designed handheld or portable reader with onboard algorithms that can calculate and display, for example, a ratio of the signal in the test device to the signal in the control device. Such an algorithm can use any measured parameter, such as, color, luminescence or fluorescence (red, green, blue, hue, saturation and so on that quantitatively represents the difference between the two tests. Alternatively, in the case of fluorescence as the signal, a handheld fluorescence flashlight comprising light emitting diodes (LEDs) of the appropriate wavelength, can also be used to visually determine a difference in intensity between the two devices.

The requirement to oxidize the sample to detect organophosphates that are inhibitory only in vivo can be overcome by using a separate enzyme wherein the mode of activity is similar to that of AChE but is inhibited by unoxidized inhibitors, such as, organophosphates (OPs). An example of such an enzyme is carboxylesterase (CE), which is inhibited by unoxidized organophosphates. Both AChE and CE react with the same substrates. In such a case, two test strips can be used, one for each enzyme.

As an alternative, a method to oxidize OPs in situ can be integrated into a test strip by the addition of a separate porous pad placed adjacent to and in communication with, such as, a sample pad containing the enzyme. The separate pad is infused with an oxidizing reagent, such as, sodium periodate, sodium hypochlorite, permanganate salts and chromate salts, among others.

Other pretreatment of a sample can be practiced by including one or more additional porous pretreatment pads adjacent to and in communication with another sited pretreatment pad or the sample pad to form a continuous fluid flow path. Thus, a pretreatment pad can serve as a filter to remove particulates and other compounds that can interfere with inhibitor binding enzyme or enzyme reacting with substrate.

Hence, the materials and methods of interest can relate to a modular test device for the detection of inhibitors of an enzyme comprising a longitudinal test strip comprising a porous sample pad on one end containing dried releasable enzyme molecules, which pad is in fluid contact and in communication with a liquid transport membrane comprising a longitudinal fluid flow path traversing, the length of the strip, and at the other end of the liquid transport membrane is another porous pad comprising a substrate associated with the enzyme, which substrate generates a detectable or measurable signal, such as, color, fluorescence, or luminescence. The method comprises the following steps: 1) a test sample fluid potentially containing an enzyme inhibitor is added in a measured uniform volume to a sample pad on one end of a strip; 2) the test sample fluid dissolving dried enzyme molecules in the sample pad, releasing same for transport to the distal end of the test strip in the flowing fluid; 3) while the fluid containing any inhibitor and the enzyme traverse the length of the strip via the liquid transport membrane, wherein any inhibitor interacts with the enzyme active sites to disable or to inactivate the enzyme and the activity thereof; 4) on reaching the distal substrate pad, active enzyme molecules will react with the substrate molecules contained in the pad to generate a measurable signal, such as, color, fluorescence, or luminescence; and 5) the test device then is read, for example, visually, for example, using a color chart as reference, or in a reader to digitally measure the amount of or intensity of a signal, for example, fluorescence, luminescence or color, generated at or about the substrate pad; wherein 6) the presence of inhibitor is deduced by a reduced level of signal generated at the distal substrate pad as compared to the signal generated by, for example, uninhibited enzyme as a negative reference comparator or a fully inhibited or a sample not containing enzyme as a positive reference comparator or 7) a positive and/or negative reference comparator value or a titration curve can be predetermined separately; or 8) a reader can display a metric, such as, a positive or negative result based on a statistically determined ratio value cutoff, or a transformed metric, such as, the ratio value defined as the measured signal of the substrate pad divided by the negative reference comparator value preloaded into an algorithm; alternatively, 9) a second strip, or more strips, can be built into the device and run simultaneously with a control, such as, a negative control fluid to generate a negative reference comparator signal in situ, wherein in) a test sample containing inhibitor generates a lower or different signal at the test substrate zone as compared to a signal of a control fluid.

The test can be conducted with concurrently tested control samples, one or plural control samples, and which can comprise a negative control which would yield higher levels of reporter as the enzyme would be free to act on the substrate; or can comprise a positive control which would yield lower levels of reporter as the inhibitor or lack of an enzyme would prevent enzymic activity with the reporter substrate, and so on. For example, plural strips can be configured to provide a titration to provide a more quantitative determination of inhibitor amount or level.

Enzymes wherein inhibitors thereof can be detected using the instant invention include, among others, esterases, such as, acetylcholinesterase, carboxylesterase and butylcholinesterase, phosphatases, such as, alkaline phosphatase, urease, glutamate dehydrogenase, tyrosinase, nitrate reductase, glucose dehydrogenase, glucose oxidase, peroxidases, such as, horseradish peroxidase, glycerol-pyrroloquinoline quinone (PQQ)-1-oxidoreductase, PQQ glucose dehydrogenase, invertase, lactate dehydrogenase, ATP synthase, β-galactosidase, organophosphate acid anhydrolase, acotinase, or any enzyme that when exposed to a substrate, inhibitor, inducer and so on, which alone or following suitable reaction, can provide a measurable or detectable signal, such as, a light, such as, a color, fluorescence, luminescence or any other detectable signal when reacted with a reporter substrate.

In embodiments, the disclosure can relate in part to a device comprising an enzyme from the esterase family, including acetylcholinesterase, butylcholinesterase, carboxylesterase, among others.

Also, the disclosure relates in part to a device comprising detectable reporter substrates, such as, N-methylindoxyl acetate (NMI), 3-(2-benzoxazolyl)umbelliferyl acetate, 8-butyryloxypyrene-1,3,6-trisulfonic acid trisodium salt, fluorescein dilaurate, 4-methylumbelliferyl acetate, 4-methylumbelliferyl butyrate, resorufin acetate, 8-octanoyloxypyrene-1,3,6-trisulfonic acid trisodium salt, derivatives thereof and so on, as a fluorogenic substrate for esterase, indoxyl acetate (IA), naphthol AS-D chloroacetate, 1-naphthyl acetate, 1-naphthyl butyrate, 4-nitrophenyl dodecanoate, 4-nitrophenyl myristate, 4-nitrophenyl octanoate, 4 nitrophenylacetate, 5-bromo-4-chloro-3-indolyl acetate, derivatives thereof and so on as a color substrate for esterases.

The disclosure relates in part to a device for rapid, on-site detection of potentially harmful inhibitors of acetylcholinesterase including, but not limited to, organophosphate, organothiophosphates and organophosphonate pesticides and toxicants, carbamate pesticides, nerve agents, heavy/toxic metals, such as, arsenic compounds, among other AChE inhibitors.

The disclosure relates in part to a device for the detection of acetylcholinesterase inhibitors of the organophosphate, organothiophosphate and organophosphonate classes, which enzyme and device do not require oxidation of the test sample. In embodiments, a device comprises a carboxylesterase (CE) in place of or in addition to an acetylcholinesterase. Thus, for such an enzyme, the reaction containers do not contain an oxidizing agent, that is, the reaction containers are free of any oxidizing agent, and there is no need for oxidation of any inhibitor prior to assay, such as, a pretreatment pad comprising an oxidizing agent.

The disclosure relates in part to a system which combines two enzymes to detect all acetylcholinesterase inhibitors without the need to oxidize the sample. The first enzyme, such as, AChE, reacts strongly with non-organothiophosphate inhibitors, such as, carbamate pesticides, but reacts weakly with non-oxidized organothiophosphates. The second enzyme, such as, CE, does react strongly with organothiophosphates, but reacts weakly with carbamates. The detection system disclosed can therefore comprise two sets of enzyme reagents, one using, for example, an esterase which may require an oxidized inhibitor, such as, AChE, and the other enzyme being one which does not require an oxidized inhibitor, such as, CE. The assay can comprise plural devices each containing a test strip for one of the enzymes. Alternatively, a single modular device can be configured to comprise plural test strips, one for each enzyme. A positive result with one or both enzymes indicates the presence of a cholinesterase inhibitor. In embodiments, a device can comprise an integrated third or more test strip(s) for one or more control samples.

In an embodiment, a modular device comprises two test strips for one enzyme. One test strip can be used with a test sample fluid while the other can be used with a control fluid as a reference comparator. Both strips can be run simultaneously. The two test strips can be configured as opposing strips in a linear orientation with the substrate pads in proximity for a simultaneous reading. Hence, the samples are added or applied at opposites ends of the device and the fluids in the separate strips migrate one to the other. Alternatively, the two test strips can be aligned side-by-side, such as, in parallel, again, with the substrate pads in proximity for a simultaneous reading of signal. Hence, the fluids in the separate strips migrate in the same direction.

The instant invention allows the detection of inhibitors, including those that belong to both the organophosphate and carbamate classes of compounds, in a simplified manner, without the required oxidation and quenching steps associated with many organophosphates and without the need to set up standard curves. Consequently, there are fewer reagents and vessels, as well as steps to practice the method of interest without the need for labile reagents, such as those requiring refrigeration, and the time to result is significantly reduced.

In an embodiment of the invention, a device comprises two test strips, one containing a first enzyme such as acetylcholinesterase and the other containing a second enzyme such as CE, for example, mounted head to head, substrate pad to substrate pad, in a holding device. The outer wells of the device are the sample wells which are placed directly above the proximal end of each strip containing the enzyme pad. To each well is added a test sample which then migrates to the distal end of each strip containing a substrate pad in the illustration above, the fluids converging in the central portion of the total device. The substrate pad of each strip is located directly underneath a viewing window or windows located in the central section of the device. One or two such windows, such as, one for each strip, is(are) centrally located on the device, which is also known as a test ticket.

In such a preferred embodiment employing esterases such as acetylcholinesterase and CE, the substrate used can be a fluorogenic substrate such as NMI, or a chromogenic substrate, such as indoxyl acetate (IA). Results can be determined visually or with the use of a reader. A negative result comprises blue color development in both central viewing windows killer about 5-10 minutes or a sufficient passage of time, which may depend on ambient temperature. A positive result comprises the lack of blue color within the same time frame in one of the viewing windows or in both windows. The lack of blue color on the substrate pad indicates that the enzyme associated with that strip has been inactivated by an inhibitor in the test sample.

Alternatively, parallel strips for multiple enzymes, such as, acetylcholinesterase. CE, and others can be put into one ticket case. In addition, a ticket case can be omitted and the test strip can be held together with a covering tape that holds the pads in place. The test strips also can be mounted in configurations previously described on a paper card with a covering tape to hold each in place or sandwiched between two paper cards with cutouts for sample addition and viewing windows.

The instant invention can be applied to the detection of inhibitors of any enzyme that requires sample pre-oxidation by the inclusion of a separate porous pretreatment pad containing oxidizing agents in fluid communication with the sample pad or any other pad in a detection device of interest. The sample pre-treatment pad also can be used for any application or method that requires sample pretreatment, such as, pre-filtration via size exclusion or using binders specific to potential interferants, pre-reduction, pre-oxidation, among others.

The instant invention is not limited to fluorescence as the measured signal, but can also use, for example, calorimetric or luminometric substrates or reaction partners as appropriate, refractive index measurements, infrared signal detection, ultraviolet signal detection and so on, the form of the detectable signal being a design choice.

BRIEF DESCRIPTION OF THE FIGURES

The following descriptions of the figures relate to non-limiting examples that depict various non-limiting embodiments exemplifying the present invention.

DETAILED DESCRIPTION OF THE INVENTION

The instant invention relates to a rapid test for exposure to inhibitors of an enzyme, such as, esterase, such as, a cholinesterase, such as, an acetylcholinesterase. The instant invention can also be applied to the detection of any inhibitor of any enzyme and to the detection of any chemical that on exposure to a reaction partner can generate a measurable signal, such as, color, fluorescence or luminescence wherein the detectable chemical is related to enzyme activity and thus can be used to assess inhibition or not of the enzyme.

A key feature of the invention is integration of all reagents required to perform the test onto a single test strip or device optionally contained in a cassette referred to, in embodiments, as a ticket. This inventive step reduces state of the art commercial kits composed of a multiplicity of reagent bottles, test tubes, labile reagents and transfer pipets to a single device and a single pipet. It is important to note that although the instant invention bears resemblance to what are called lateral flow assays (LFAs) or more formally, immunochromatographic assays, the underlying principle is substantively different. Whereas LFAs require antibodies and/or antigens for use as capture and/or detector reagents with some of these components imprinted as immobilized test zones on a porous longitudinal membrane similar to the fluid transfer membrane of the instant invention, the test method described herein requires no antibodies or antigens and no immobilized test zones imprinted on the fluid transfer membrane. It is therefore not an LFA as known in the immunology art.

For the purposes of non-limiting description of the invention, a detailed description of the rapid test for esterases is provided. Esterases are essential for normal nervous system function. Some toxins act by inhibiting esterase activity, such as, a cholinesterase, such as, an acetylcholinesterase activity. Depressed AChE activity causes, for example, aberrant synapse function. Thus, acetylcholinesterase (AChE) is an enzyme that degrades (through its hydrolytic activity) the neurotransmitter, acetylcholine, producing, choline and an acetate group. AChE can be found at neuromuscular junctions and in cholinergic synapses where AChE activity serves to terminate synaptic transmission. AChE is found in all animal species. As a reagent, AChE can be obtained and purified from any of several sources, such as, insects, eels, cows, and pigs. AChE also is available in recombinant form.

Carboxylesterase (CE) belongs to the family of carboxylic ester hydrolases which are widely found in nature. The enzyme catalyzes the hydrolytic cleavage of the ester bond in a carboxylic ester to form an alcohol and a carboxylic acid. This is the exact same hydrolysis reaction catalyzed by AChE reacting specifically with acetylcholine. As a reagent, CE can be isolated from many sources such as bacilli, rabbits, and pigs.

Both AChE and CE have common substrates, one of which is NMI, which when hydrolyzed, produces acetic acid and N-methyl-3-hydroxyindole, which emits fluorescence which can be detected on exposure to UV radiation, for example, at 380 nm or 405 nm, as known in the art.

To detect potentially harmful compounds that can inhibit AChE, a test procedure involves exposing a measured limiting amount of AChE to a sample that potentially contains an inhibitor. Inhibitor molecules in the sample can interact with the active sites of the enzyme and deactivate the enzyme. Subsequent reaction with a substrate reporter will show reduced enzyme activity (for example, lower fluorescence signal) when compared to a non-inhibited enzyme.

For the purposes of the invention as relating to esterases, such as, AChE, inhibitors can be classified as carbamates, organophosphates, organothiophosphates, organophosphonates, their derivatives and other compounds that can attach to the serine hydroxyl group of an active site of an AChE. That reaction of inhibitor and enzyme blocks the neurotransmitter, acetylcholine, from interacting with the enzyme and resulting in cholinergic hyperactivity and loss of neurotransmitter control of the nervous system.

Most of the compounds that inhibit AChE do so without the need for metabolic transformation or chemical change. Certain organophosphates, however, do not exhibit inhibitory activity in vitro but do so in vivo only after a physiological oxidation of the phosphate moiety has occurred, such as, with organothiophosphates that require the thiophosphate group to undergo in vivo oxidation to a phosphate group. An example is methamidophos which is not detectable by such methods unless oxidized. Test methods have therefore required a sample preparation step involving oxidation with a follow-on quenching of the unused oxidizing agent. Hence, the invention relates in part to a method that obviates the need for oxidation and quenching. By using a second enzyme, such as, CE, which can be deactivated by unoxidized organophosphates, the need for an oxidizing agent is obviated.

An alternative solution to the need for oxidation is to add a separate porous pad containing dried oxidizing agent above, adjacent to at least in communication with the sample pad so that on addition of a test sample to the porous pad comprising oxidizing agent, the inhibitor that may be in the sample will be exposed to the oxidizer prior to or as mixed with the enzyme contained in the sample pad.

The invention can comprise a system or testing system for detection of enzyme inhibitors comprising, in part, a device of such dimensions as to be handheld, which device contains one or more test strips as previously described. When one test strip is used, the signal generated on the substrate pad can be visually compared to a level of signal associated with an uninhibited enzyme that is known or stored in a data base. Such signal can be printed on a reference sheet, or stored electronically in a reader. When two test strips are used, the first strip can be used to test an unknown sample and the second strip can be used to run a control fluid in order to compare the signal generated with the unknown sample with that generated with a control fluid on the same device. A device can contain more than two strips so that multiple samples can be tested simultaneously, multiple controls can be run simultaneously or both. The advantage of such a design with an on-board control reference is that the test can be run at a wider range of temperatures and environmental conditions without losing accuracy and sensitivity since each test is self-calibrated.

Enzyme substrates of interest are those that serve a reporter function and in some embodiments, the reporter is one which can be readily detected by a device or by mere visual inspection, which can be, for example, fluorogenic substrates that yield a fluorescence that can be visualized with the unaided eye, such as, NMI, chromogenic substrates, such as, IA, that yield a detectable or visible color, or luminogenic substrates. Reaction zones comprise porous matrices that have been uniformly treated with substrate such that one reaction zone is similar to the other in terms of the total amount of dry substrate contained. Examples of porous matrices include membranes, celluloses, glass fibers, cotton, nylon, composites, spun polymers, among others.

The sample pad at the upstream end of the test strip can be a porous matrix that releasably holds enzyme molecules in the dry state. Methods to enable reversible binding are known and include pretreating the porous matrix with passivating materials such as proteins and sugars that can strongly adhere to the external and internal surfaces of the matrix. Such treated matrices, after drying, can then be loaded with enzyme molecules such that the enzyme does not adhere strongly to the matrix and are therefore is releasable or is dissolvable on addition of a fluid sample. Examples of porous matrices include membranes, celluloses, glass fibers, cotton, nylon, composites, spun polymers, patterned microchannels on a plastic, glass, a metal surface, among others.

The test device can be of any size and shape, such as to be held comfortably and stably in the hand, or such size and proportion as to compatibly fit in a receptacle of a purpose-built reader which detects the reporter and so on as a design choice. The reader can be of such size and proportions as to be handheld. The test device can be inserted into a designated receptacle in this reader such that the test zones comprising the substrate pads are efficiently exposed, in the case of a fluorogenic substrate, to light sources at the excitation wavelength of the product of the enzyme-substrate reaction and a camera or similar light or signal-gathering device that can measure the intensity of the emitted signal or save an image of the reaction site. An alternative design can use a chromogenic substrate that can be measured at the wavelength maximum of the colored enzyme-substrate reaction product.

In some circumstances, the test system can relate to one where the enzyme comprises an esterase. Examples of esterases include acetylcholinesterase, butylcholinesterase or carboxylesterase. In some embodiments, the test system is one where the substrate comprises an N-methyl indoxyl acetate (NMI) or an indoxyl acetate (IA). In certain embodiments, the test system detects inhibitors such as, an organophosphate, an organothiophosphate, an organophosphonate or a carbamate. Other inhibitors include a pesticide, a toxicant or a nerve agent. Advantageously, the test system of interest does not require oxidation of a test sample.

Hence, the invention can relate in part to a method for detecting an inhibitor of an enzyme comprising: a) adding an aliquot of a fluid sample to as sample well of a device or the sample pad of a test strip, b) allowing sufficient time for the fluid to dissolve and to mobilize dried enzyme on the porous sample pad, and for fluid to traverse along the longer axis of a longitudinal membrane, allowing the migrated fluid to saturate the substrate pad at the distal end, and to develop on or at that substrate pad a measurable signal or reporter as a product of the reaction of enzyme and substrate, such as, color, fluorescence, or luminescence on or at that pad; and c) obtaining a value comprising the amount of signal generated where an inhibitor is correlated with a lower amount of signal. The signal can be measured by a reader or can be assessed visually. The data obtained from the reader can be assessed in a qualitative manner, that is, a visual inspection reveals an observable difference between a positive sample and a negative sample. In embodiments, the signal obtained by the reader relating to the amount of reporter in a reaction zone is digitized and that data are processed to yield a quantitative value or can be processed to yield a metric, for example, a normalized value that accounts for background levels and so on, as known in the art. Thus, in embodiments, the data manipulation is one where the value from the sample is divided by the value oldie background or of a control to yield a ratio or index. Thus, the reader obtained value is compared to a statistically determined ratio value cutoff, which can be a population mean value or a historical value determined by collating historical data, for determining or distinguishing a positive result from a negative result.

After sufficient amount of time, the device is inserted into a reader. The detector senses and captures the signal from the reaction site or zone and that signal is digitized into a manipulable and storable form. An onboard algorithm can be used to transform the signal or digitized data which can be stored, manipulated and so on, for example, to provide a ratio of the signal at the test reaction zone to that on the control zone, in the case of a 2-strip device. Alternatively, a ratio can be calculated using a stored standard signal value, such as a populational mean value or average value as a reference. An artisan can select an algorithm as a design choice to provide a corrected value, a relative value, an adjusted value and so on of the amount of reporter in the test sample thereby providing a more accurate determination of the amount of reporter present, wherein said amount of reporter provides a correlation to the amount of inhibitor in the original sample.

The signal that is measured by the reader can be, for example, color, fluorescence or luminescence as determined by the substrate. The signal can be parsed or analyzed using detectors of differing specificity and sensitivity, such as, level of red color, green, blue, the hue or a color, luminance, saturation and so on. The numerical values associated with each channel can be used to generate a ratio of the test sample signal to a control signal. A channel or a combination of channels can be used to calculate a ratio result. The choice of channel(s) is dependent on the sensitivity the chosen channel(s) confers on the test.

Figure 1:
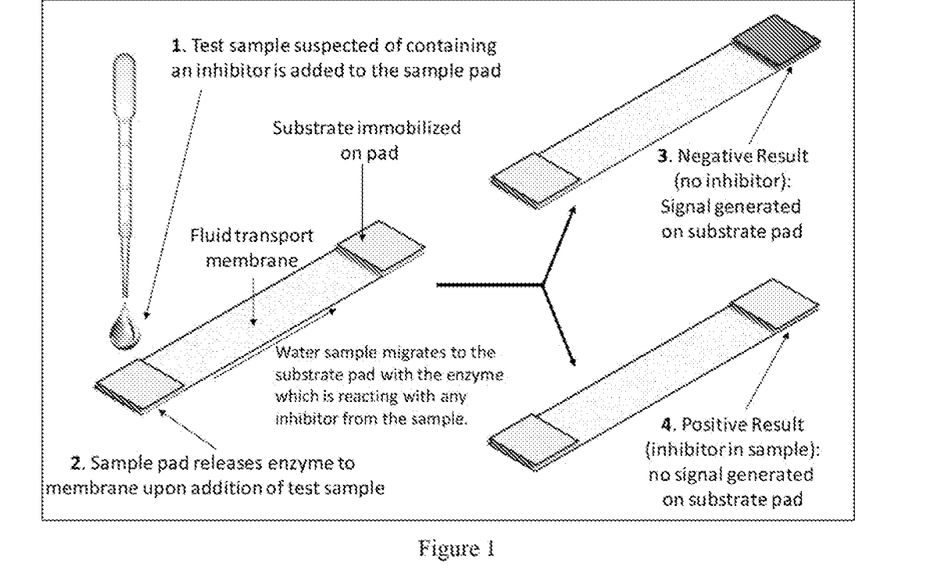
FIG. 1 depicts a test procedure for detection of enzyme inhibitors, for example, in a water sample. A fixed uniform volume of an unknown water sample suspected of containing an enzyme inhibitor is added to the sample pad on a test strip. The water sample dissolves and releases the dried enzyme in the sample pad, allowing the enzyme to react with any inhibitor present in the water sample and allowing the enzyme to flow with the water as the liquid contacts the fluid transfer membrane. The aqueous reaction mixture travels through the transfer membrane to the substrate pad containing, for example, a chromogenic, fluorogenic or luminogenic substrate of the enzyme. During this period, the inhibitor can react with enzyme active sites to disable activity of the enzyme. When the fluid front reaches the substrate pad, any uninhibited enzyme will react with the reporter substrate molecules to generate a signal, such as, a color or fluorescence. If there is inhibitor in the sample, the signal generated is lower, less intense or non-existent as compared to the signal of a sample comprising an uninhibited enzyme.
Figure 2:
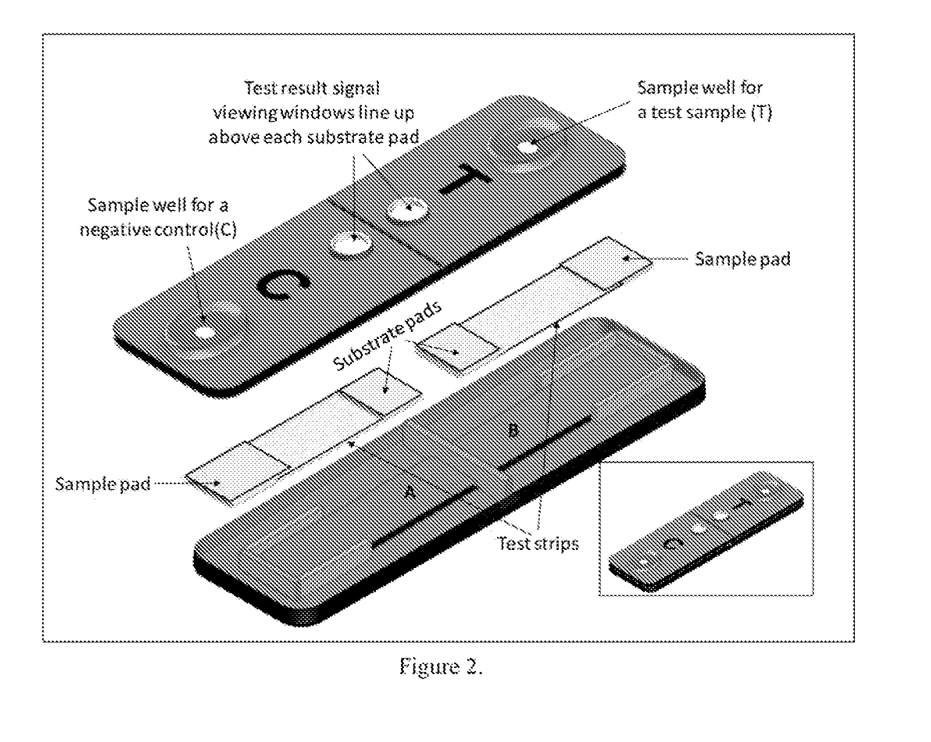
FIG. 2 shows a blow-up schematic of a rapid test device or test ticket with a negative reference comparator test strip integrated with a sample test strip. The inset shows the assembled ticket. The intensity of the test sample signal is compared to that of the negative control. A significantly lower signal in the test (marked T in the figure) viewing window as compared to the signal in the control viewing window (marked C in the figure) denotes presence of an inhibitor in the test sample.
Figure 3:
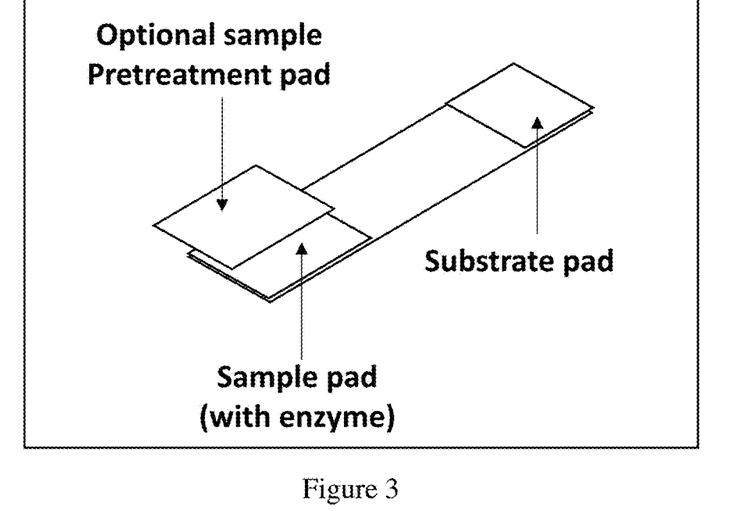
FIG. 3 shows how a sample pretreatment step, such as, oxidation of organophosphates, can be integrated in the 1-step test ticket by positioning a porous pad containing a pretreatment reagent, such as, an oxidizer, above the sample pad containing releasable enzyme, although other configurations are possible as a design choice.
Figure 4:
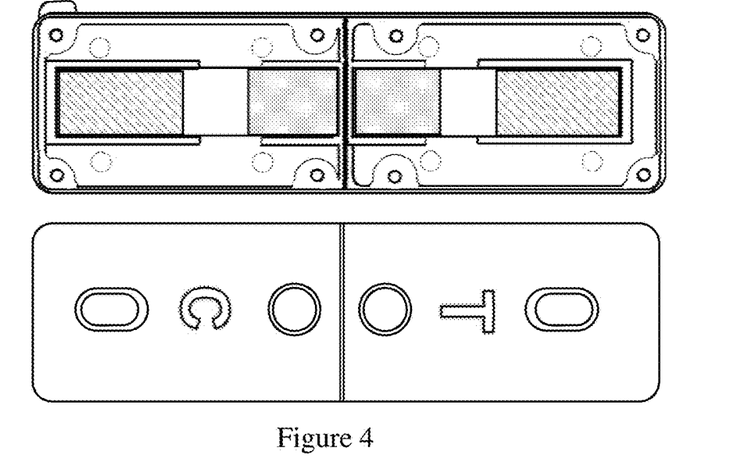
FIG. 4 shows an example of a test device composed of a top piece (left) and a bottom piece (right) containing two test strips. The top piece is assembled to marry with the bottom piece to form a test device securing, the test strips within.
Figure 5:
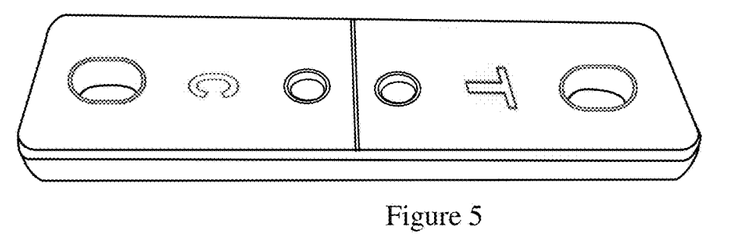
FIG. 5 provides the assembled test device of the components depicted in FIG. 4.

FIGS. 4 and 5 provide further exemplifications of a test device via a non-limiting example of a ticket assembly designed to contain two test strips, one for a negative control sample and the other for a test sample, comprising a top and bottom piece. The top piece is divided into two halves, each containing four openings. The opening at each end is a sample well into which a uniform volume of fluid sample (test sample or control sample) is added. These openings sit directly on top of or over the sample pads containing the enzyme. The two openings in the middle are test result viewing windows that sit directly on top of or over the substrate pads of each of the tickets. The bottom piece holds two test strips placed head to head (substrate pad to substrate pad) in fitted slots. In an embodiment, the two test strips are oriented side-by-side. The substrate pads of each test strip can be in proximity so that the two zones where the respective substrate is converted to a detectable signal can be compared and/or read simultaneously. In embodiments, the sample addition sites of the two test strips are separate for each test strip. In embodiments, a single sample addition site is used by both or adjacent test devices, there, the single sample addition site is configured to channel fluid to sample pads of both or plural adjacent test strips.

A multiplicity of test strips can also be mounted in parallel in a device to run multiple tests simultaneously. There is no limitation to the number of test strips in such a device other than the requirement of being of a size and conformation for integration into a reader for measuring the generated signals.

The instant invention can comprise an onboard comparator which is a control reaction zone. The control reaction zone will contain the fluorescence, color, luminescence or other signal associated with a known positive and/or negative sample. The signal generated in the test sample reaction zone is compared to the signal at the Control reaction zone. When using a negative control, significant difference in signal between these two reaction zones is evidence of a positive result, indicating that the test sample does contain an inhibitor.

The fluids that can be tested using the instant invention can be any liquid sample that can solubilize or suspend inhibitors. Non-limiting examples include water, blood fractions, such as, serum and plasma, cerebrospinal fluid, amniotic fluid, other physiological fluids and various solvents. Generally a solvent has a lower vapor pressure to ensure capillary flow of the fluid along the length of the test strip. The fluids can also comprise extracts of solid mixtures or gels to which inhibitors have been added, dispersed or encapsulated within. Such samples can be made compatible for analysis using the instant invention by appropriate extraction, lysis and clean-up procedures known in the art.

A, "reader," or, "reading device," comprises an electromechanical device that provides the ability to detect and to measure an appropriate signal, such as fluorescence, light, a color, and so on. A reader can comprise a sensing device for detecting a signal, such as a camera, a photomultiplier tube, a scanner, and so on. The reader can contain a processor-controlled device to manipulate the sensing device, the sample or a carrier or holding device of one or more samples and so on to enable detecting a plurality of sites or samples at one time or consecutively in a defined order. The reader can be configured as a component of a robotic system that introduces an article of manufacture, for example, the ticket, that carries the sample, or the carrier, for example, comprising two or more test strips, into the reading device, and then removes the article of manufacture when the detecting is completed. Spectrophotometers, fluorimeters, luminometers, and so on are examples of readers or reading devices.

The instant invention as applied to the detection of, for example, AChE inhibitors also can comprise the use of a test device in which reaction zones comprising substrate pads to which, for example, N-methylindoxyl acetate (NMI) or IA has been immobilized. AChE enzyme is dried on a pad comprising a passivated porous matrix. A negative water sample or buffer can be used as the negative control. The test procedure follows the previously described steps.

The instant invention as applied to the detection of AChE further can comprise a second set of reagents using a second enzyme, such as, carboxylesterase (CE). As previously described, AChE and CE can react with the same substrates, and in one embodiment for the detection of AChE inhibitors, can react with the same fluorogenic substrate, NMI. Whereas AChE is strongly reactive with most inhibitors, such as oxidized organophosphates and carbamates, AChE is weakly reactive with unoxidized organothiophosphates. On the other hand, enzymes, such as, CE, can be inhibited by organothiophosphate inhibitors without the need for oxidation and quenching, but is weakly reactive with other AChE inhibitors, such as, carbamates. Thus, by using these two kinds of enzyme reagents, a test method for the detection of all AChE inhibitors can be produced that requires no oxidation and quenching steps. A positive result with one or both enzymes indicates the presence of an inhibitor in the test sample.

The sensitivity and time to result of the method can be manipulated by changing the length of the fluid transfer membrane, porosity of the membrane or both, for example. The time it takes for the fluid to reach the substrate pad can be prolonged, to give an inhibitor more time to diffuse to the enzyme active site and disable the site, or shortened to effect a faster time to result. For example, highly porous membranes allow a faster passage of fluid from one end to the other, while low porosity membranes reduce that rate. For example, membranes, such as, Millipore Hi-Flow membranes, for example, HF090, HF120, HF135, HF180 and so on, have varying pore size and hence enable varying now rate. Additionally, glass fiber or cotton pads from GE Whatman with capillary flow rates ranging from 10 s/4 cm to 50 s/4 cm also can be utilized for controlling flow rate. The assay read time can range from 1 mm to 30 mm, or more. A suitable reaction time for quick diagnosis would be a read time between 30 seconds and 10 minutes. Higher reaction temperatures can shorten the reaction time. Hence, by varying the membrane type, length, thickness and so on, an artisan can configure a device of interest to provide results in a suitable time as a design choice.

Optimal amounts of enzyme to be placed on/in the sample pad, optimal amounts of substrate to be placed on/in the substrate pad, and the optimal length and porosity of the fluid transfer membrane can be determined by practicing the materials and methods taught herein as a design choice. For example, enzyme solutions can be prepared at 0.1 U/mL, to 20 U/mL concentrations and substrate solutions can be prepared at 0.1 mg/mL to 50 mg/mL concentrations. Generally, the reactions are optimal at a pH of from about 6 to about 9 and thus, the reagent solutions are prepared at about that pH or at a pH suitable for the particular reagent using, for example, phosphate, borate, Tris and other buffers, at various concentrations, as known in the art. Pads can be prepared in any manner, for example, reagents can be spotted on membranes or pads; or, larger sizes of membranes or pads can be immersed in the reagent solution and cut into appropriately sized pieces, generally, after drying, for assembly in the ticket.

The substrate can be applied to the porous matrix directly or indirectly as known in the art. Hence, a solution of substrate can be applied to the porous matrix and then the matrix is dried. A linker or a molecule that binds substrate can be applied to the porous matrix, such as by drying or using a chemical process, such as, derivatizing the matrix to enable binding of the linker or binding molecule thereto to yield a modified porous matrix, which modified matrix then is exposed to the substrate to enable the substrate to be bound by the linker or binding molecule.

As to the enzyme, such are commercially available, for example, in dry form, and thus can be added directly to the substrate pads in a buffered solution then dried. Any buffer salts, proteins, sugars for release and stabilizers and the like can be added to this enzyme preparation. The test strips or tickets are stored under such preferred conditions to retain enzyme activity. Enzymes whose inhibitors can be detected can include, among others, esterases such as acetyl cholinesterase, carboxylesterase, butylcholinesterase, alkaline phosphatase and other phosphatases, urease, glutamate dehydrogenase, tyrosinase, nitrate reductase, glucose dehydrogenase, glucose oxidase, horseradish peroxidase, glycerol-(PQQ)-1-oxidoreductase, PQQ glucose dehydrogenase, invertase, lactate dehydrogenase. ATP synthase, beta-galactosidase, organophosphate acid anhydrolase, acotinase, or any enzyme that can generate measurable color, fluorescence, or luminescence when reacted with a substrate.

In most cases, an oxidizer is not needed. However, for those targets that may require oxidation, oxidizers, such as, sodium hypochlorite, sodium perchlorate, sodium periodate, sodium chlorite, chlorine, chlorine dioxide, a chloramine, sodium dichloroisocyanurate, bromine, iodine, sodium persulfate, oxygen, ozone, hydrogen peroxide (with or without an iron catalyst), hydrogen peroxide-urea (carbamide peroxide), polyvinylpyrrolidone supported hydrogen peroxide, benzoylperoxide, ultraviolet light, electric discharge and so on, can be used prior to testing with the ticket device of interest.

In light oldie known reaction conditions under which enzyme and substrate operate, a sample may be treated to have a pH of between 6 and 9, for example, by dissolving in or mixing with a suitable buffer.

The materials and methods of interest now will be exemplified in the following non-limiting examples.

EXAMPLES

Example 1. Preparation and Treatment of Substrate Pad

N-methyl indoxyl (NMI) acetate (100 mg, Sigma-Aldrich) was dissolved in 100 mil, 100% USP ethyl alcohol (Sigma-Aldrich) for a final concentration of 3 mg/mL. Strips of porous matrix Surewick Sample Pad C248 (Millipore) were saturated with this NMI solution and dried at 45° C. for two hours. The strips were then removed from the oven and stored in a resealable plastic bag with desiccant.

Other substrate pads were constructed similarly using an appropriate solvent with indoxyl acetate, naphthol AS-D chloroacetate, 1-naphthyl acetate, 1-naphthyl butyrate, 4-nitrophenyl dodecanoate, 4-nitrophenyl myristate, 4-nitrophenyl octanoate, 4 nitrophenylacetate and 5-bromo-4-chloro-3-indolyl acetate.

Example 2. Preparation of AChE Sample Pad

AChE from eel (Sigma-Aldrich) was dissolved to a final concentration of 2.2 units/mL in a buffer containing 10 mM potassium phosphate, 5% sucrose and 0.5% BSA at pH=7.4 and passed through a 0.22 µm filter. Strips of Millipore GFCP20300 glass fiber were pretreated by soaking with a mixture of 2% sucrose and 2% Triton in 6.25 mM borate buffer and dried at 45° C. in an oven for 2 hours. These glass fiber strips were then saturated with the solution of AChE and dried for 2 hours at 45° C. The strips were then removed from the oven and stored in a resealable plastic bag with desiccant.

Example 3. Preparation of CE Sample Pad

CE from rabbit liver was dissolved to a final concentration of 1.28 units/mL in a buffer containing 10 mM potassium phosphate, 5% sucrose and 0.5% BSA at pH=7.4 and passed through a 0.22 µm filter. Strips of Millipore GFCP20300 glass fiber were pretreated by soaking, with a mixture of 2% sucrose and 2% Triton in 6.25 mM borate buffer and dried at 45° C. in an oven for 2 hours. These glass fiber strips were then saturated with the solution of CE and dried for 2 hours at 45° C.

Example 4. Card Assembly and Test Ticket Preparation

To an adhesive-coated plastic backing, card (G&L) cut to 3×27 cm, is attached the fluid transfer membrane (nitrocellulose membrane) at a distance of 10 mm from the card bottom edge. The enzyme sample pad is attached flush to the bottom edge of the backing card overlapping the nitrocellulose membrane strip. The substrate pad is then attached flush to the other edge of the backing card (top edge), overlapping the nitrocellulose membrane. The assembled cards are then cut into 6.75 mm wide×16 mm long test strips using an automated guillotine cutter. The test strips of each enzyme type are placed in the test ticket device as shown in FIG. 4.

Example 5. Detection of AChE Inhibitors Using the Instant Invention

A stock solution (1 mg/mL) of the carbamate pesticide, oxamyl (Supelco), was prepared in methanol, then serially diluted in purified water to a final concentration of 0.1 mg/L for use as a test sample. A 0.1 mL volume of this test sample was added to the test sample well ("T") of an AChE test ticket. As a negative control, 0.1 mL of purified (RO) water was added to the control sample well of the same ticket.

Similarly, a stock solution (1 mg/mL) of the organophosphate pesticide, fenamiphos (Supelco), was prepared in methanol, then serially diluted in purified water to a final concentration of 0.5 mg/L for use as a test sample. A 0.1 mL volume of this test sample was added to the test sample well ("T") of a CE test ticket. As a negative control, 0.1 mL of purified (RO) water was added to control sample well of the same ticket.

To represent a negative sample, RO water was added to a test well of each enzyme type ticket (AChE and CE) and to the control well of each ticket as well.

Figure 6:
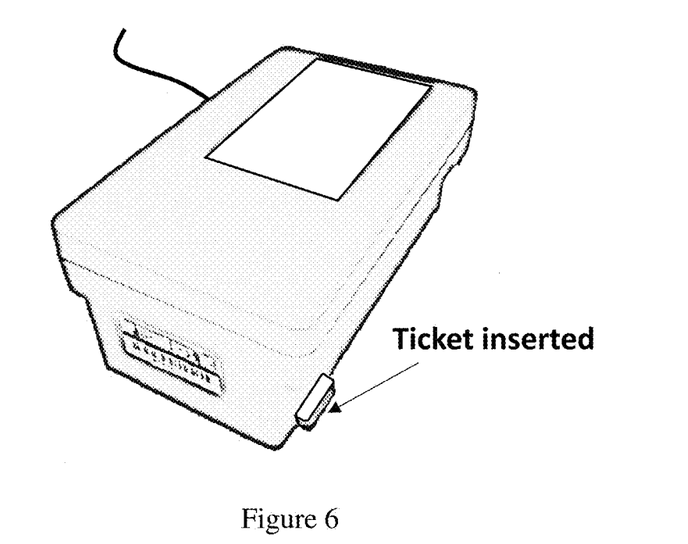
FIG. 6 is an image of a handheld reader designed to measure the fluorescence in the two middle windows of the tickets depicted in FIGS. 2, 4, and 5. A ticket is shown inserted in the read site of the reader.

All tickets were then allowed to run for 15 minutes, then were inserted into a reader comprised of low light color cameras, 400 nm UV LED and custom color analysis software (FIG. 6). The reader calculates a ratio of the hue measured in the test sample site at the substrate pad to the hue measured in the negative control site at the substrate pad. Enzyme inhibition was deduced by a difference in the hue measurement of the test sample as compared to that of the negative control. Based on a statistical calculation of total system error, a ratio greater than 1.25 is considered positive. A ratio below 0.125 is considered negative.

Figure 7:
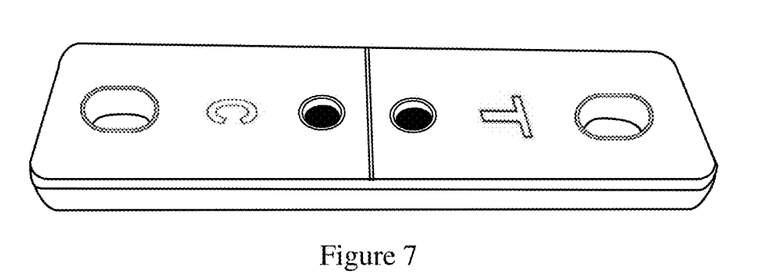
FIG. 7 shows a typical negative test result examined visually outside the handheld reader. Both test sites show color.
Figure 8:
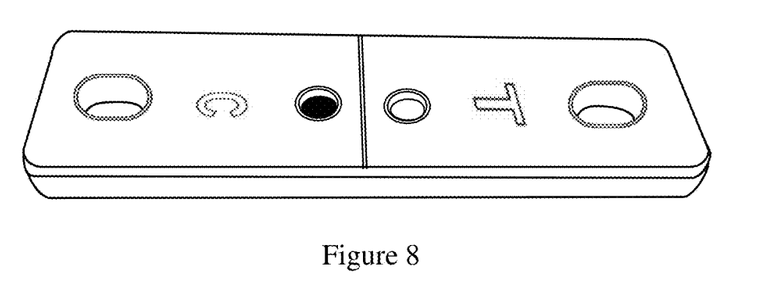
FIG. 8 shows a typical positive test result examined visually outside the handheld reader. The control site shows color while the test, site remains white.
Figure 9:
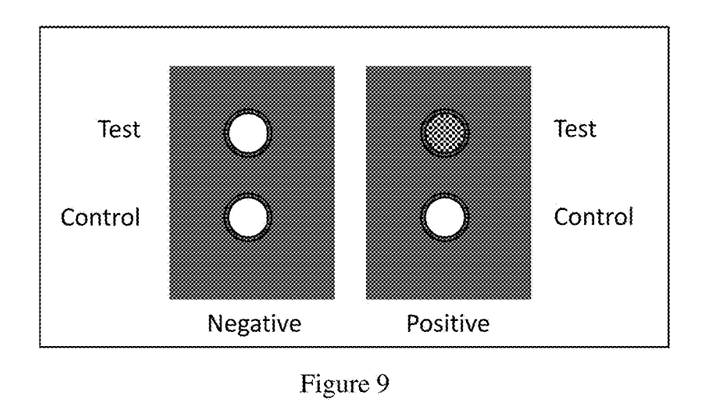
FIG. 9 shows images for positive and negative test ticket results as displayed by the reader. Note that the degree of signal on the control and test sites of the negative ticket show similar levels of signal while the positive ticket shows signal in the control site and no signal in the test site.
Figure 10:
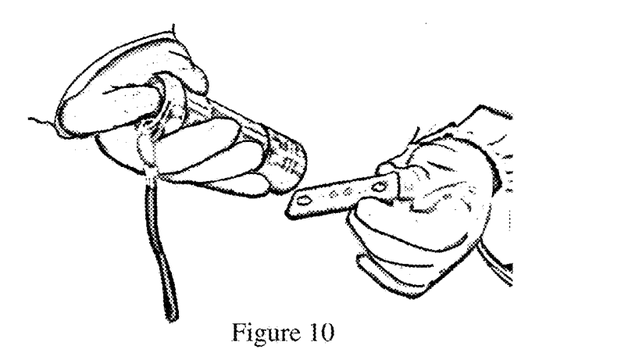
FIG. 10 demonstrates the use of a UV flashlight as a source of excitation energy to visualize test results without a reader.
Figure 11:
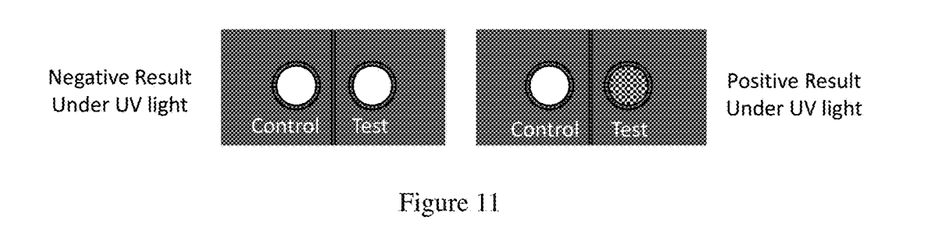
FIG. 11 depicts test results visualized under a UV flashlight.
Figure 12:
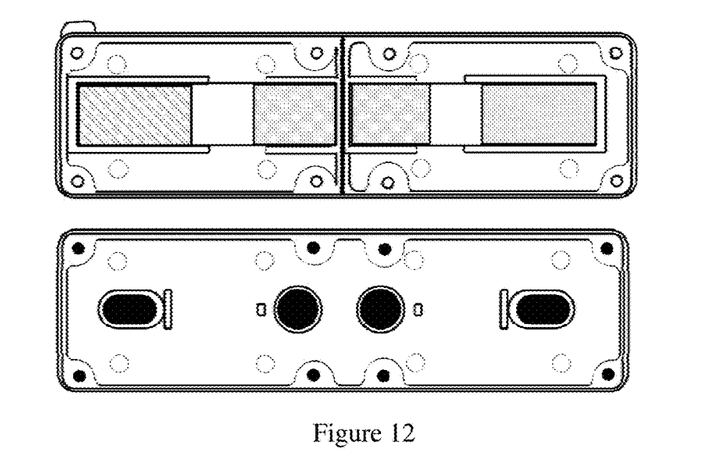
FIG. 12 depicts a colorimetric test ticket containing two strips mounted head to head as shown, one strip uses acetylcholinesterase and the other strip uses CE.
Figure 13:
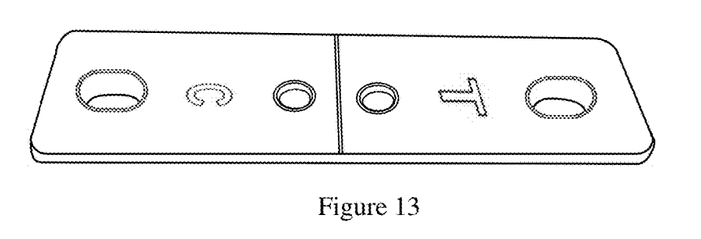
FIG. 13 is an external view of the assembled test ticket comprising the two outer sample wells and the two central viewing window's.
Figure 14:
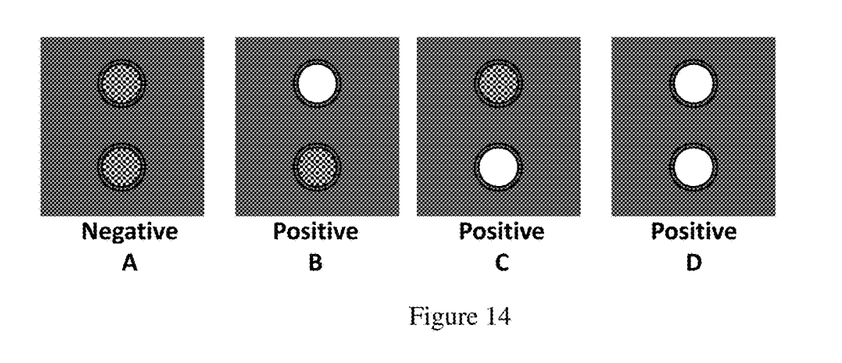
FIG. 14 shows possible results that can be obtained using the colorimetric test ticket of FIGS. 12 and 13. A shows a negative result wherein both enzymes are not inhibited by the test sample. B and C are positive results wherein one or the other enzyme is inhibited by the test sample. B shows the result with 1 ppm fenamiphos, which inhibits CE, while C shows the result with 1 ppm oxamyl, which inhibits acetylcholinesterase. D is a positive result wherein both enzymes are inhibited by the test sample, which can result when potent nerve agents are present in the test sample.

It was found that inhibition of the enzyme, demonstrated by the lack of formation of the highly fluorescent product, N-methyl-3-hydroxyindole, could be detected visually under UV flashlight illumination as well. Analysis was alternatively performed by visual observation of the ticket using a 400 nm UV LED flashlight (FIGS. 7 and 8). Visually, inhibition was detected directly based on a decrease in fluorescence of the test sample as compared to that of the negative control.

Visual detection was achieved using a colorimetric substrate, such as, indoxyl acetate. Other substrates that can be used include naphthol AS-D chloroacetate, 1-naphthyl acetate, 1-naphthyl butyrate, 4-nitrophenyl dodecanoate, 4-nitrophenyl myristate, 4-nitrophenyl octanoate, 4 nitrophenylacetate, 5-bromo-4-chloro-3-indolyl acetate and derivatives thereof.

Table 1 exemplifies results obtained when testing water containing pesticides at an amount that approximates the Human Lethal Concentration (HLC) of each. Oxamyl is a carbamate pesticide that reacts strongly with AChE while fenamiphos is an organothiophosphate pesticide that, without oxidation, reacts more strongly with CE than with AChE

TABLE 1

Results using a test sample well:control well hue ratio cutoff of 1.25 in the rapid test for AChE inhibitors. The data were generated by the reader.

| Pesticide | mg/L | Fluorescence hue ratio | Result |
|---|---|---|---|
| RO Water | NA | 0.97* | Negative |
| RO Water | NA | 1.02** | Negative |
| Oxamyl | 0.1 | 2.82* | Positive |
| Fenamiphos | 0.5 | 2.94** | Positive |

*tested with AChE
**tested with CE

References cited herein are herein incorporated by reference in entirety.

REFERENCES

Mahajna Mahmoud and Casida John E "Oxidative Bioactivation of Methamidophos Insecticide: Synthesis of N-Hydroxymethamidophos (A Candidate Metabolite) and its Proposed Alternative Reactions Involving N→O Rearrangement or Fragmentation through a Metaphosphate Analogue", Chem. Res. Toxicol, 11, 26-34, 1998

Özlem Faizl, Ahmet Colakl, Nagihan Saglam, Sabriye Çanakçi and Ali Osman Beldüz, 2007 "Determination and Characterization of Thermostable Esterolytic Activity from a Novel Thermophilic Bacterium Anoxybacillus gonensis A4", Journal of Biochemistry and Molecular Biology, Vol. 40, No. 4, July 2007, pp, 588-594

Timo Hamers, Kim R. J. Molin, Jan H. Koeman, and Albertinka J. Murk "A Small-Volume Bioassay for the Quantification of the Esterase Inhibiting Potency of Mixtures of Organophosphate and Carbamate Insecticides in Rainwater: Development and Optimization", Toxilogical Sciences, 58, 60-67 (2000)

Craig E. Wheelock, Guormin Shan and James Ottea "Overview of Carboxylesterases and Their Role in the Metabolism of Insecticides", J. Pestic. Sci., 30(2), 75-83 (2005)

Craig E. Wheelock, Bryn M. Phillips, Brian S. Anderson, Jeff L. Miller, Mike J. Miller, and Bruce D. Hammock, D. M. Whitacre (ed.), "Applications of Carboxylesterase Activity in Environmental Monitoring and Toxicity Identification Evaluations (TIEs)", Reviews of Environmental Contamination and Toxicology. 195:117-178, 2008

Yuske Amaki, Edgard E. Tulin, Shunsaku Ueda, Kuio Ohmiya, and Tsunco Yamane "Purification and Properties of a Thermostable Esterase of *Bacillus stearothermophilus* Produced by recombinant *Bacillus brevis*", Biosci. Biotech. Biochem., 56 (2), 238-241, 1992

"Techniques to Detect insecticide Resistance Mechanisms (Field and Laboratory Manual)", WHO/CDS/CPC/MAL/98.6, World Health Organization Department of Disease Prevention & Control WHO Communicable Diseases (CDS)

Cheryl L. Beseler, Lorann Stallones, Jane A. Hoppin, Michael C. R. Alavanja, Aaron Blair, Thomas Keefe, and Freya Kamel "Depression and Pesticide Exposures among Private Pesticide Applicators Enrolled in the Agricultural Health Study" Environmental Health Perspectives 116, 1713-1719, 2008

Wang A, Costello S, Cockburn M, Zhang X, Bronstein J and Ritz B. "Parkinson' disease risk from ambient exposure to pesticides." Eur. J. Epidemiol. 26(7), 547-55, 2011

Elbaz A, Clavel J, Rathouz P J, Moisan F, Galanaud J P, Delemotte B, Alperovitch A, Tzourio C. "Professional exposure to pesticides and Parkinson's disease" Ann Neurol. 22(4), 494-504, 2009

We claim:

1. A device for detecting an inhibitor of an enzyme comprising a longitudinal test strip enabling flow of fluid from one end to the other, comprising two pads of porous matrices on either end of said test strip and a fluid transfer membrane between the pads along the length of said test strip in liquid communication with each pad, one of said two pads comprising an upstream pad comprising a sample pad comprising releasably dried said enzyme, and second of said two pads comprising a downstream substrate pad comprising an immobilized substrate of said enzyme, wherein said substrate comprises a reporter which, on reaction with said enzyme, produces a signal in said device detectable visually or with a portable device, and said inhibitor reacts with said enzyme to form an inactivated enzyme that does not react with said substrate; wherein said device does not comprise an antibody and/or an antigen as a capture site.

2. The device of claim 1, wherein said enzyme comprises an esterase.

3. The device of claim 1, wherein said enzyme comprises acetylcholinesterase, butylcholinesterase or carboxylesterase.

4. The device of claim 1, wherein said substrate comprises N-methylindoxyl acetate (NMI), 3-(2-benzoxazolyl)umbelliferyl acetate, 8-butyryloxypyrene-1,3,6-trisulfonic acid trisodium salt, fluorescein dilaurate, 4-methylumbelliferyl acetate, 4-methylumbelliferyl butyrate, resorufin acetate, 8-octanoyloxypyrene-1,3,6-trisulfonic acid trisodium salt, indoxyl acetate, naphthol AS-D chloroacetate, 1-naphthyl acetate, 1-naphthyl butyrate, 4-nitrophenyl dodecanoate, 4-nitrophenyl myristate, 4-nitrophenyl octanoate, 4 nitrophenylacetate, 5-bromo-4-chloro-3-indolyl acetate or derivatives thereof.

5. The device of claim 1, wherein said enzyme comprises a phosphatase, a urease, a glutamate dehydrogenase, a tyrosinase, a nitrate reductase, a glucose dehydrogenase, a glucose oxidase, a peroxidase, a glycerol-pyrroloquinoline quinone (PQQ)-1-oxidoreductase, a PQQ glucose dehydrogenase, an invertase, a lactate dehydrogenase, an ATP synthase, a galactosidase, an organophosphate acid anhydrolase or an acotinase.

6. A composition comprising the device of claim 1 and a liquid sample suspected of containing said inhibitor.

7. The composition of claim 6, wherein said inhibitor comprises an organophosphate, an organothiophosphate, an organophosphonate, a carbamate, a heavy metal or a toxic metal.

8. The composition of claim 6, wherein said inhibitor comprises a pesticide, a toxicant or a nerve agent.

9. The composition of claim 6, wherein said liquid sample comprises a water for human consumption, a source water from natural and man-made bodies of water, an ocean, a wash of an edible product or a wipe of a surface.

10. A method for detecting an inhibitor of an enzyme using the device of claim 1 comprising:
   a) adding an aliquot of a fluid sample suspected of containing an inhibitor of said enzyme to a sample pad at a proximal end of a test strip comprising said enzyme in dissolvable and releasable form,
   b) enabling the fluid sample to dissolve said enzyme, creating a reaction mixture of said enzyme and any inhibitor in the sample and enabling any inhibitor to interact with the enzyme to disable activity thereof,
   c) enabling said reaction mixture to contact and to traverse a fluid transfer membrane of said test strip to the distal end of said membrane to a substrate pad comprising a substrate reporter, and
   d) enabling uninhibited enzyme in said reaction mixture to react with said substrate reporter to generate a detectable signal.

11. The method of claim 10, wherein said test strip is contained in a device to hold the test strip, the device comprising an opening or sample well located above the sample pad through which a fluid test sample is introduced and a window directly above the substrate pad for viewing the reporter.

12. The method of claim 10, wherein a sample pretreatment pad is positioned above said sample pad.

13. The method of claim 12, wherein said pretreatment pad comprises a size-exclusion filter.

14. The method of claim 12, wherein said pretreatment pad comprises an oxidizing agent.

15. The method of claim 10, further comprising (e) engaging said test strip with a reader to measure amount of reporter.

16. The method of claim 15, wherein said reader comprises an algorithm for providing a corrected or relative amount of reporter.

17. The method of claim 10, further comprising at least one additional test strip, each additional test strip comprising a sample pad, a fluid transport membrane and a substrate pad.

18. The method of claim 17, further comprising one additional test strip and adding a second sample or a control sample to said sample pad of said one additional test strip.

* * * * *